US005458120A

United States Patent [19]

Lorraine

[11] Patent Number: 5,458,120

[45] Date of Patent: Oct. 17, 1995

[54] ULTRASONIC TRANSDUCER WITH MAGNETOSTRICTIVE LENS FOR DYNAMICALLY FOCUSSING AND STEERING A BEAM OF ULTRASOUND ENERGY

[75] Inventor: Peter W. Lorraine, Schenectady, N.Y.

[73] Assignee: General Electric Company, Schenectady, N.Y.

[21] Appl. No.: 162,988

[22] Filed: Dec. 8, 1993

[51] Int. Cl.[6] ..................................................... A61B 8/00

[52] U.S. Cl. ..................................... 128/663.01; 73/642

[58] Field of Search .................................. 333/147, 149; 310/334; 367/7; 128/660.07, 660.01, 662.03, 663.01; 73/642, 644

[56] References Cited

U.S. PATENT DOCUMENTS

| | | | |
|---|---|---|---|
| 3,674,945 | 7/1972 | Hands | 310/8.3 |
| 3,967,233 | 6/1976 | Maguer et al. | 340/3 R |
| 4,217,684 | 8/1980 | Brisken et al. | 29/25.35 |
| 4,425,525 | 1/1984 | Smith et al. | 310/336 |
| 4,433,291 | 2/1984 | Yariv et al. | 324/244 |
| 4,441,503 | 4/1984 | O'Donnell | 128/660 |
| 4,470,305 | 9/1984 | O'Donnell | 73/626 |
| 4,924,503 | 5/1990 | Klein | 381/190 |
| 4,986,808 | 1/1991 | Broadwin et al. | 604/22 |
| 4,991,151 | 2/1991 | Dory | 367/150 |
| 4,993,416 | 2/1991 | Ophir et al. | 128/660.06 |

*Primary Examiner*—Francis Jaworski

*Attorney, Agent, or Firm*—Enrique J. Mora; Marvin Snyder

[57] ABSTRACT

An ultrasonic transducer with a magnetostrictive lens for dynamically focussing and steering a beam of ultrasound energy is provided. The magnetostrictive lens is operable in response to a magnetic field generated by a coil such that the speed of propagation of the ultrasound beam is selectively controlled as the beam passes through the lens. The lens can be made up of first and second prisms wherein at least one of such prisms is magnetostrictive. Alternatively, the lens can be made up of an individual stage made of a composite having a plurality of elongated rods of magnetostrictive material cooperating in response to the control signal applied to the lens for selectively controlling the propagation speed of the ultrasound beam passing therethrough.

25 Claims, 1 Drawing Sheet

ULTRASONIC TRANSDUCER WITH MAGNETOSTRICTIVE LENS FOR DYNAMICALLY FOCUSSING AND STEERING A BEAM OF ULTRASOUND ENERGY

BACKGROUND OF THE INVENTION

This invention relates to ultrasonic transducers and, more particularly, to an ultrasonic transducer with a magnetostrictive lens for dynamically focussing and steering a beam of ultrasound energy.

Ultrasonic transducers for medical or industrial applications are constructed from one or more piezoelectric elements sandwiched between a pair of electrodes. Such piezoelectric elements are typically constructed of lead zirconate titanate (PZT), polyvinylidene difluoride (PVDF), or PZT ceramic/polymer composite. The electrodes are connected to a voltage source, and when a voltage is applied, the piezoelectric elements are excited at a frequency corresponding to that of the applied voltage. When a voltage pulse is applied, the piezoelectric element emits an ultrasonic beam into the media to which it is coupled at the frequencies contained in the excitation pulse. Conversely, when an ultrasonic beam strikes the piezoelectric element, the element produces a corresponding voltage across its electrodes. Typically, the front of the element is covered with an acoustic beam matching layer that improves the coupling with the media in which the ultrasonic beams propagate. In addition, a backing material is disposed to the rear of the piezoelectric element to absorb ultrasonic beams that emerge from the back side of the element so that they do not interfere. A number of such ultrasonic transducer constructions are disclosed in U.S. Pat. Nos. 4,217,684, 4,425,525, 4,441,503, and 4,470,305, all of which are assigned to the instant assignee.

When used for ultrasound imaging, the transducer typically has a number of piezoelectric elements arranged in an array and driven with separate voltages (apodizing). By controlling the time delay (or phase) and amplitude of the applied voltages, the ultrasonic beams produced by the piezoelectric elements combine to produce a net ultrasonic beam focused at a selected point. By controlling the time delay and amplitude of the applied voltages, this focal point can be selectively moved in a plane to scan the region of interest to be imaged.

This form of ultrasonic imaging is referred to as "phased array sector scanning", or "PASS". The PASS technique is comprised of a series of measurements in which the steered ultrasonic beam is transmitted into the region of interest. A system using the PASS technique then switches to a receive mode after a short time interval, and the reflected ultrasonic beam is received and stored. Typically, the transmission and reception are steered in the same direction during each measurement to methodically acquire data from a series of focal points along a scan line. The time required to conduct the entire scan is a function of the time required to make each measurement and the number of measurements required to cover the entire region of interest at the desired resolution and signal-to-noise ratio. For example, a total of 128 scans lines may be acquired over a 90 degree sector, with each scan line being steered in increments of 0.70°. A number of such ultrasonic imaging systems are disclosed in U.S. Pat. Nos. 4,155,258, 4,155,260, 4,154,113, 4,155,259, 4,180,790, 4,470,303, 4,662,223, 4,669,314 and 4,809,184, all of which are assigned to the instant assignee.

Although PASS techniques provide significant inspection capability, implementing such dynamic focussing usually requires a large number of electronic components to impart the time delays (and/or phase shifts) to the signals from each transducer array element. The use of such large number of electronic components significantly adds to the cost and complexity of the imaging system. In an effort to reduce the number of electronics components such PASS techniques may sometimes require moving the transducer relative to the region of interest. In this case use of a manipulator, to provide such relative movement between the transducer and the region of interest, may be required which similarly adds to the complexity and cost of the system. Thus, there is need in the art to provide an improved ultrasonic transducer which is capable of dynamically focussing and steering a beam of ultrasonic energy in a manner which does not require use of either a large number of electronic components or of a manipulator and thus effectively reduces the cost and complexity required to achieve dynamic focussing and steering of beams of ultrasound energy. Moreover, the transducer of the present invention can be conveniently used as an adjunct in present systems using such PASS techniques to provide three-dimensional scanning of the region of interest to be imaged.

SUMMARY OF THE INVENTION

Generally speaking, the present invention fulfills the foregoing needs by providing an ultrasonic transducer which can be conveniently used for an imaging system. The ultrasonic transducer comprises a transducer element which generates a beam of ultrasound energy propagating along a transducer axis with a predetermined speed of propagation. A magnetostrictive lens is acoustically coupled to the transducer element and has an input face positioned at an angle with respect to the transducer axis to receive and to pass the beam of ultrasound energy. The magnetostrictive lens is operable such that the speed of propagation of the ultrasound beam is selectively controlled as the ultrasound beam passes through the lens. The transducer typically includes means, such as a coil, for applying a control signal, i.e., a magnetic field, to the magnetostrictive lens, thereby selectively controlling the propagation speed of the ultrasound beam. The lens can be comprised of first and second prisms positioned on the transducer axis to share a mutually interfacing surface. At least one of such first and second prisms is made of a respective magnetostrictive material, preferably a composite of suitable magnetostrictive materials such as Terfenol or Metglass 2605SC alloys, responsive to the control signal generated by the coil.

Alternatively, the lens may be comprised of an individual stage made up of a composite having a plurality of elongated rods of magnetostrictive material respectively extending substantially parallel to the transducer axis. The plurality of rods in the composite advantageously cooperates in response to the control signal to selectively control the propagation speed of the ultrasound beam passing therethrough. In one exemplary embodiment, the lens can have an output face having a substantially planar surface and the lens is operable such that the beam of ultrasound energy is selectively steered at a predetermined angle θ based upon the control signal applied to the lens. In another exemplary embodiment the output face of the lens can have a curved surface substantially centered relative to the transducer axis and the curved output face is designed so that the lens is operable in response to the control signal in a manner that allows the beam of ultrasonic energy to be dynamically focused at a controllable range. Thus, it should be appreciated that the present invention provides for dynamic steering and focusing of ultrasound energy in a more economical fashion than presently available techniques have permitted heretofore.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description in conjunction with the accompanying drawings in which like characters represent like parts throughout the drawings, and in which:

DETAILED DESCRIPTION OF THE INVENTION

Figure 1:
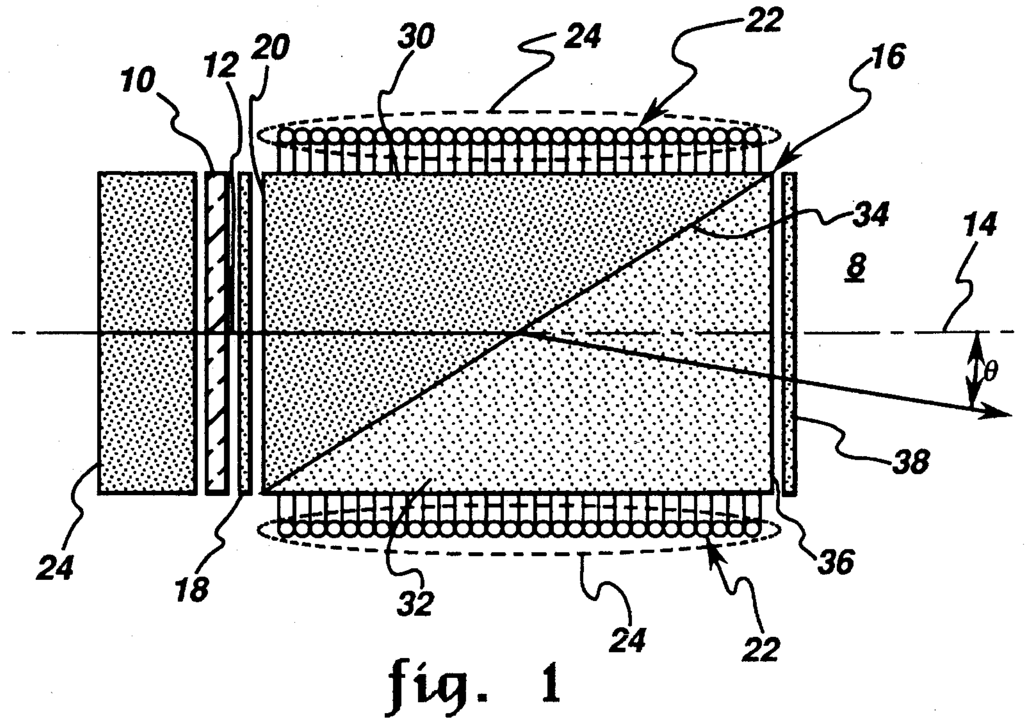
FIG. 1 shows a cross section of an ultrasonic transducer with an exemplary magnetostrictive lens in accordance with an embodiment of the present invention.

FIG. 1 shows an ultrasonic transducer 8 for an imaging system (not shown). The transducer includes a piezoelectric transducer element 10 as generally described in the background section of the present disclosure. Transducer element 10 generates a beam of ultrasound energy 12 which initially propagates along a transducer axis 14 with a predetermined speed of propagation. A magnetostrictive lens 16 is acoustically coupled to the transducer element either directly or though a first beam matching layer 18 positioned forward of the transducer element 10. In either case, an input face 20 of the lens 16 is positioned at an angle, such as 90°, with respect to the transducer axis to receive and to pass the beam of ultrasound energy through the magnetostrictive lens. As will be explained shortly hereafter, the magnetostrictive lens is operable such that the speed of propagation of the beam is selectively controlled as the beam of ultrasound energy passes through the lens.

Figure 2:
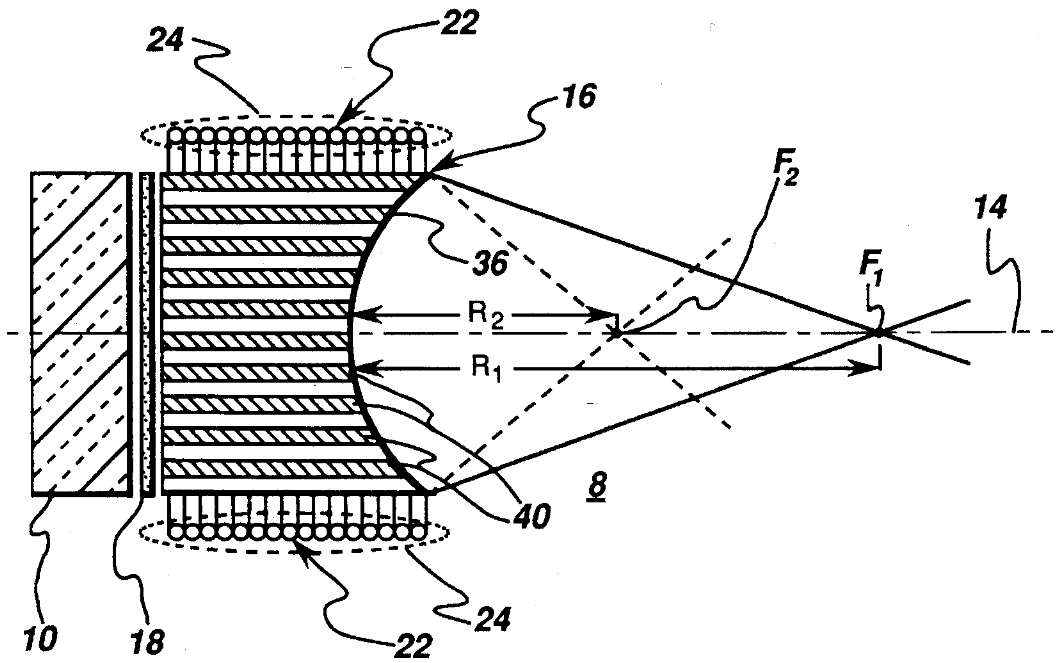
FIG. 2 shows a cross section of another embodiment of the ultrasonic transducer of the present invention.

As depicted in FIGS. 1 and 2, the lens 16 can be suitably surrounded by means, such as a conventional coil 22, for applying a control signal 24 to the lens 16. The conventional coil 22 or other such electromagnetic device is designed to generate a variable magnetic field when energized by a conventional electrical power source (not shown). The variable magnetic field generated by conventional coil 22 is electromagnetically coupled with lens 16 and constitutes the control signal applied to the lens 16.

As will be appreciated by those skilled in the art, the phenomenon of magnetostriction, that is, the change in shape and size of a body whenever its state of magnetization is changed, has been observed in numerous materials. In particular, due to magnetostriction the elastic properties of certain alloys such as Terfenol alloy (approximate formulation $Tb_{0.3}\ Dy_{0.7}\ Fe_2$) and Metglass 2605SC alloy; and rare earth compounds such as $TbFe_2$ have demonstrated significant dependence on the level of the magnetic field applied to such materials. For instance in the case of the Terfenol alloy, the Young's Modulus of elasticity has been observed to increase by up to at least 2.5 times from an unexcited state, that is, the state corresponding to the level of the magnetic field applied to the material being zero, to a magnetic saturation state. Since the coefficient of elasticity of a given material can be shown to be directly related to the speed of propagation of sound passing therethrough, the foregoing property can be advantageously exploited to dynamically vary the speed of propagation of the beam of ultrasound energy passing therethrough by varying the level of the control signal applied to the given material, i.e., varying the level of magnetic field which causes the material to change its coefficient of elasticity. In particular, the longitudinal velocity of sound passing through a typical bulk isotropic material is given by:

$$Cl=\sqrt{\frac{E}{\rho}} \quad \text{Eq. (1)}$$

where ρ is the density of the material and E is the coefficient of elasticity corresponding to the longitudinal direction of propagation. Since lens 16 is made of a magnetostrictive material, such as the foregoing exemplary alloys, which typically responds to the applied magnetic field H as follows:

$$S=\Delta L/L=CH^2 \quad \text{Eq. (2)}$$

wherein S is a percentage change in the longitudinal dimension for a given material and C is the magnetostriction coefficient for such given material and therefore lens 16 can be operable such that the speed of propagation of the sound beam passing therethrough is selectively controlled in response to the level of the control signal applied to the lens by coil 22. For example, in the Terfenol alloy, the Young's Modulus of elasticity has been observed to increase by up to at least 2.5 times from the unexcited state with a resulting speed of propagation change of at least 60% in a magnetic field of 5 kOe. Conversely, in the Metglass 2605SC alloy, the Young's Modulus of elasticity has been observed to decrease by at least 10 times from an unexcited state which can result in a speed of propagation change of up to 300% in a magnetic field of 1 Oe.

As shown in FIG. 1, lens 16 may be comprised of first and second prisms 30 and 32 wherein at least one of the prisms is made of a respective magnetostrictive material, preferably a composite, responsive to the magnetic field produced by coil 22. The first and second prisms are positioned in the transducer axis to share a mutually interfacing surface 34. In operation, when beam of ultrasound energy 12 passes through the interfacing surface 34, since at least one of the prisms is responsive to the magnetic field generated by coil 18, such magnetostrictive prism will impart a predetermined change to the propagation speed of the beam passing therethrough which in turn causes beam 12 to have a predetermined angular deviation θ relative to the transducer axis. The choice of the particular material for the magnetostrictive prism depends on the particular design implementation, however, preferred typical materials that can be used include composites of the foregoing alloys such as Terfenol alloy and Metglass 2605SC alloy, the latter available from Allied Signal, Inc. The choice of the particular material for the remaining prism, if any, which can be nonresponsive to the applied control signal can be conveniently chosen to optimize the acoustical refraction change at the interfacing surface as well as to provide suitable acoustical coupling for the sound beam passing therethrough.

As seen in FIG. 1, lens 16 includes an output face having a substantially planar surface 36 positioned at a predetermined angle, such as 90°, relative to the transducer axis. A second beam matching layer 38 can be positioned forward of the output face of the lens to provide a suitable acoustical matching impedance to the beam passing therethrough. The actual value for the matching impedance being chosen depending on the specific nature of the medium upon which the beam of ultrasound energy is transmitted into. Thus, the embodiment shown in FIG. 1 can be effectively used to selectively steer at a predetermined angle θ the beam of ultrasound energy generated by transducer element 10 based upon the level of the control signal applied to the magnetostrictive lens, that is, based upon the level of the magnetic field applied to the lens. Thus, it should be appreciated that such dynamic steering of ultrasound beams can now be accomplished in accordance with the present disclosure without having to use the large number of transducer elements and associated electronics typically required of systems using PASS techniques. Hence, a key advantage of the present invention is the relatively simplicity by which such dynamic steering can be effectively implemented.

In the embodiment shown in FIG. 2, it can be seen that the output face of the lens has a curved surface 36 substantially centered relative to the transducer axis 14. The curved surface, cooperates to provide a predetermined focal point $F_1$ at a predetermined range $R_1$, during the unexcited state for example. In operation, the level of the control signal applied to the lens can be varied such as to provide dynamic focussing at a selectable range such as exemplary focal point $F_2$ at a corresponding range $R_2$. Thus, the embodiment of FIG. 2, conveniently provides dynamic focussing at a selectable range for the beam of ultrasound energy passing therethrough without having to use the complex time or phase delay electronics typically required of systems using PASS techniques. As seen in FIG. 2, lens 16 can be comprised of an individual stage made up of a composite having a plurality of elongated rods 40 of magnetostrictive material respectively extending substantially parallel to the transducer axis. The plurality of rods in the composite cooperates, in response to the control signal applied thereto, to selectively control the propagation speed of the ultrasound beam passing therethrough. The foregoing composite construction using Metglass 2605SC rods, for example, can advantageously provide at least a three times reduction for the longitudinal speed of propagation for the ultrasound beam passing therethrough. It will be appreciated by those skilled in the art that the foregoing composite construction could also be used in the embodiment shown in FIG. 1. For instance, either one of the first and second prisms could have been constructed using such composite construction. Further, it will be appreciated that the second beam matching layer 38 shown in FIG. 1 can be conveniently shaped to match the curved output face of the lens and can be positioned forward of such output face to provide a suitable acoustical matching impedance to the beam passing therethrough.

Although various specific constructions have been given for the present invention, it is to be understood that these are for illustrative purposes only. Various modifications and adaptations will be readily apparent to those of skill in the art. In view of these and other modifications, the scope of the present invention should be determined by reference to the claims appended hereto.

What is claimed:

1. An ultrasonic transducer for an imaging system comprising:

a transducer element which generates a beam of ultrasound energy propagating along a transducer axis with a predetermined speed of propagation; and a magnetostrictive lens acoustically coupled to said transducer element and having an input face positioned at an angle with respect to said transducer axis to receive and to pass said beam of ultrasound energy, said magnetostrictive lens operable such that said speed of propagation of said beam is selectively controlled as said beam passes through said lens.

2. The ultrasonic transducer of claim 1 further comprising means for applying a control signal to said magnetostrictive lens, thereby selectively controlling said propagation speed.

3. The ultrasonic transducer of claim 2 wherein said lens includes an output face having a substantially planar surface positioned at a predetermined angle relative to said transducer axis.

4. The ultrasonic transducer of claim 3 wherein said beam of ultrasound energy is selectively steered at a predetermined angle θ based upon said control signal applied to said magnetostrictive lens.

5. The ultrasonic transducer of claim 2 wherein said lens includes an output face having a curved surface substantially centered relative to said transducer axis.

6. The ultrasonic transducer of claim 5 wherein said magnetostrictive lens is operable in response to said control signal such that said beam of ultrasound energy is dynamically focused at a controllable range.

7. The ultrasonic transducer of claim 2 wherein said magnetostrictive lens is comprised of first and second prisms positioned in said transducer axis to share a mutually interfacing surface.

8. The ultrasonic transducer of claim 7 wherein at least one of said first and second prisms is made of a respective magnetostrictive material responsive to said control signal.

9. The ultrasonic transducer of claim 8 wherein at least one of said first and second prisms is made of a composite having a plurality of elongated rods of magnetostrictive material respectively extending substantially parallel to said transducer axis, said plurality of rods in said composite cooperating in response to said control signal to selectively control said propagation speed.

10. The ultrasonic transducer of claim 2 wherein said magnetostrictive lens is substantially comprised of an individual stage made of a composite having a plurality of elongated rods of magnetostrictive material respectively extending substantially parallel to said transducer axis, said plurality of rods in said composite cooperating in response to said control signal to selectively control said propagation speed.

11. The ultrasonic transducer of claim 2 further comprising a beam backing layer positioned rearward of said transducer element.

12. The ultrasonic transducer of claim 11 further comprising a first beam matching layer interposed between said transducer element and said input face of said lens.

13. The ultrasonic transducer of claim 12 further comprising a second beam matching layer positioned forward of said output face of said lens.

14. An ultrasonic transducer for an imaging system comprising:

a transducer element which generates a beam of ultrasound energy propagating along a transducer axis with a predetermined speed of propagation;

a magnetostrictive lens acoustically coupled to said transducer element and having an input face positioned at an angle with respect to said transducer axis to receive and to pass said beam of ultrasound energy, said magnetostrictive lens operable such that said speed of propagation of said beam is selectively controlled as said beam passes through said lens; and means for applying a control signal to said magnetostrictive lens, thereby selectively controlling said propagation speed.

15. The ultrasonic transducer of claim 14 wherein said lens includes an output face having a substantially planar surface positioned at a predetermined angle relative to said transducer axis.

16. The ultrasonic transducer of claim 15 wherein said beam of ultrasound energy is selectively steered at a predetermined angle θ based upon said control signal applied to said magnetostrictive lens.

17. The ultrasonic transducer of claim 14 wherein said lens includes an output face having a curved surface substantially centered relative to said transducer axis.

18. The ultrasonic transducer of claim 17 wherein said magnetostrictive lens is operable in response to said control signal such that said beam of ultrasound energy is dynamically focused at a controllable range.

19. The ultrasonic transducer of claim 14 wherein said magnetostrictive lens is comprised of first and second prisms positioned in said transducer axis to share a mutually interfacing surface.

20. The ultrasonic transducer of claim 19 wherein at least one of said first and second prisms is made of a respective magnetostrictive material responsive to said control signal.

21. The ultrasonic transducer of claim 20 wherein at least one of said first and second prisms is made of a composite having a plurality of elongated rods of magnetostrictive material respectively extending substantially parallel to said transducer axis, said plurality of rods in said composite cooperating in response to said control signal to selectively control said propagation speed.

22. The ultrasonic transducer of claim 14 wherein said magnetostrictive lens is substantially comprised of an individual stage made of a composite having a plurality of elongated rods of magnetostrictive material respectively extending substantially parallel to said transducer axis, said plurality of rods in said composite cooperating in response to said control signal to selectively control said propagation speed.

23. The ultrasonic transducer of claim 14 further comprising a beam backing layer positioned rearward of said transducer element.

24. The ultrasonic transducer of claim 23 further comprising a first beam matching layer interposed between said transducer element and said input face of said lens.

25. The ultrasonic transducer of claim 24 further comprising a second beam matching layer positioned forward of said output face of said lens.

* * * * *